United States Patent [19]

Tomioka

[11] Patent Number: 5,256,818
[45] Date of Patent: Oct. 26, 1993

[54] METHOD FOR MAKING β-MERCAPTOPROPIONIC ACID

[76] Inventor: Tetsuzo Tomioka, 24-11, Senriyama Nishi 6-chome, Suita-shi, Osaka-fu, Japan

[21] Appl. No.: 790,369

[22] Filed: Nov. 12, 1991

[30] Foreign Application Priority Data

Nov. 19, 1990 [JP] Japan .................................. 2-314795
Nov. 19, 1990 [JP] Japan .................................. 2-314796

[51] Int. Cl.$^5$ .......................................... C07C 148/00
[52] U.S. Cl. ..................................... 562/512; 560/147
[58] Field of Search ...................... 562/512; 560/147

[56] References Cited

U.S. PATENT DOCUMENTS 3,927,085  12/1975  Zengel et al. ........................ 562/512

FOREIGN PATENT DOCUMENTS 58-198460  5/1982  Japan .
63-6545    1/1988  Japan ................................... 562/512
2082174    2/1982  United Kingdom ................ 562/512

*Primary Examiner*—José G. Dees
*Assistant Examiner*—Keith MacMillan
*Attorney, Agent, or Firm*—Tilton, Fallon, Lungmus & Chestnut

[57] ABSTRACT

A novel method for making β-mercaptopropionic acid which comprises adding alkaline hydroxide to thiodipropionic acid to obtain alkaline thiodipropionate, mixing thus obtained alkaline thiodipropionate with an aqueous solution of alkaline sulfide, then reacting the mixed solution with addition of heating in a required time, and acidifying the reacted solution with a strong acid.

2 Claims, No Drawings

METHOD FOR MAKING β-MERCAPTOPROPIONIC ACID

FIELD OF THE INVENTION

This invention relates to a method for making β-mercaptopropionic acid (HSCH₂CH₂COOH), and more particularly, relates to a method of getting a high productivity of β-mercaptopropionic acid by reacting alkaline thiodipropionate obtained from thiodipropionic acid, or contained in the reaction solution of acrylonitrile and excess of alkaline hydrosulfide or sulfide, with alkaline sulfide.

BACKGROUND OF THE INVENTION

As β-mercaptopropionic acid is suitable for cross-linking agents for acrylic ester polymer, hardening agents for epoxy resin and the like, the production of β-mercaptopropionic acid has recently increased rapidly. Relating to the production of β-mercaptopropionic acid, there have been known several methods for making the acid by chloridizing a starting material, and by using thiourea or sodium hydrosulfide, e.g., in Japanese Patent Open Publication No. 198460/83. Correspondingly, I have already proposed a new making method by reacting acrylonitrile with sodium sulfide, in the presence of free sodium hydroxide, as disclosed in Japanese Patent Publication No. 6545/88 (i.e., Japanese Patent No. 1458518). This method is much economical because the process of production is simpler and also the time required for the total reaction is shorter than the known method mentioned above using acrylonitrile and sodium hydrosulfide.

According to my method described in Japanese Patent Publication No. 6545/88, ammonia gas, mirabilite solution and thiodipropionic acid are prepared evidently as by-products. When this ammonia gas is absorbed into water, it changes available pure ammonia solution, and when this mirabilite solution is crystallized on cooling, the crystal can be used directly to several different applications. When this thiodipropionic acid is also esterized with 2-ethyl hexyl alcohol, stearyl alcohol or the like, the ester has previously been useful as stabilizers for polypropylene or antioxidants for several synthetic resins. However, with respect to these applications, the demand of thiodipropionic acid has a decreasing tendency because another low-priced chemical compound is beginning to be used recently. It is probable that the disposal of thiodipropionic acid becomes difficult in the future.

SUMMARY OF THE INVENTION

This invention provides a novel method for making β-mercaptopropionic acid by using alkaline thiodipropionate obtained direct from thiodipropionic acid isolated in the solid state, or contained in the resultant solution in a process of production of β-mercaptopropionic acid. In the former case, the method comprises adding alkaline hydroxide to thiodipropionic acid, mixing thus obtained alkaline thiodipropionate with an aqueous solution of alkaline sulfide, reacting the mixed solution with addition of heating, and acidifying the resultant solution with a strong acid. If adding excess of alkaline hydroxide, the reaction of alkaline thiodipropionate and the aqueous solution of alkaline sulfide may take place in the presence of residual alkaline hydroxide. In the latter case, the method comprises reacting acrylonitrile with excess of an aqueous solution of alkaline hydrosulfide, adding furthermore excess of alkaline hydroxide to the reacted solution, reacting the by-product with alkaline sulfide formed by reacting residual alkalines hydrosulfide and hydroxide, in the presence of residual alkaline hydroxide, with addition of heating, and acidifying the resultant solution with a strong acid. Instead of excess of alkaline hydroxide, excess of alkaline sulfide may be used.

It is therefore an object of the invention to provide a novel method for making β-mercaptopropionic acid of which the demand has still an increasing tendency, from thiodipropionic acid of which the demand has a decreasing tendency.

It is another object of the invention to provide a novel method that gets a high productivity of β-mercaptopropionic acid by reacting alkaline thiodipropionate with alkaline sulfide.

It is still another object of the invention to provide a novel method in which the amount of low-priced alkaline hydroxide used increases, while the quantity of high-priced alkaline sulfide consumed decreases.

It is yet another object of the invention to provide a method in which converts alkaline thiodipropionate formed as a by-product when acrylonitrile is reacted with excess of alkaline hydrosulfide or sulfide, into alkaline β-mercaptopropionate.

These and other objects, features and advantages of the invention will become more apparent to those skilled in the art from the following description.

DESCRIPTION OF THE INVENTION

In the method according to the invention, as the starting material thiodipropionic acid ($S(CH_2CH_2COOH)_2$), or acrylonitrile and excess of alkaline hydrosulfide or sulfide are employed.

In the former case that the starting material is thiodipropionic acid isolated in the solid state, this acid may preferably be a by-product formed usually in my method disclosed in Japanese Patent Publication No. 6545/88. It also may be a by-product formed in another known method or obtained in order to employ herein.

Alkaline hydroxide used in order to convert this thiodipropionic acid into the alkaline salt is generally sodium or potassium hydroxide or the like. Alkaline sulfide that reacts with alkaline thiodipropionate is, for example, sodium or potassium sulfide or the like. The alkaline sulfide may be employed in a high concentration state of an aqueous solution by dissolving the solid in water with addition of heating. Alternately, the sulfide may be formed by mixing alkaline hydrosulfide, a sufficiency of alkaline hydroxide and water by heating. The reaction by adding alkaline dithiopropionate direct to a high concentration of an aqueous solution of alkaline sulfide may be carried out completely at a heating temperature of usually 110° to 130° C. for one or several hours, as in the following:

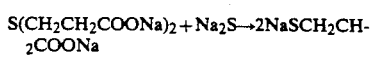

$$S(CH_2CH_2COONa)_2 + Na_2S \rightarrow 2NaSCH_2CH_2COONa$$

The alkaline thiodipropionate is converted into alkaline β-mercaptopropionate by reacting effectively with somewhat small quantity of alkaline sulfide, preferably in the presence of residual alkaline hydroxide. In this case, it can assume that the residual alkaline hydroxide has catalytic action, and thus the yield of alkaline β-mercaptopropionate becomes higher.

β-mercaptopropionic acid is prepared by acidifying the resultant solution with a strong acid such as sulfuric or hydrocholoric acid, as follows:

$$NaSCH_2CH_2COONa + H_2SO_4 \rightarrow HSCH_2CH_2COOH + Na_2SO_4 \text{(recovery)}$$

In the latter case that the starting material is acrylonitrile and excess of alkaline hydrosulfide or sulfide, alkaline hydrosulfide or sulfide is sodium or potassium hydrosulfide or sulfide and alkaline hydroxide is sodium or potassium hydroxide in a practical manner. Generally, alkaline hydroxide may be added gradually after acrylonitrile has been reacted with alkaline hydrosulfide or sulfide. Alternately, it may be added simultaneously at the start of the reaction of acrylonitrile and alkaline hydrosulfide or sulfide. As this result, it can assume that alkaline β-mercaptopropionate is formed in the following reaction steps:

$$CH_2=CHCN + NaSH \rightarrow NaSCH_2CH_2CN \text{ or}$$

$$CH_2=CHCN + Na_2S + H_2O \rightarrow NaSCH_2CH_2CN + NaOH$$

$$NaSCH_2CH_2CN + NaOH + H_2O \rightarrow NaSCH_2CH_2COONa + NH_3\text{(recovery)}$$

In the case employing excess of alkaline hydrosulfide, it is possible that alkaline sulfide is formed by reacting residual alkalines hydrosulfide and hydroxide that remain in the reacted solution.

$$NaSH + NaOH \rightarrow Na_2S + H_2O$$

Alkaline thiodipropionate generates simultaneously when the objective, i.e., alkaline β-mercaptopropionate is formed. The alkaline thiodipropionate is also converted into alkaline β-mercaptopropionate by reacting with alkaline sulfide, in the presence of residual alkaline hydroxide that remains in the reacted solution, as in the following:

$$S(CH_2CH_2COOH)_2 + Na_2S \rightarrow 2NaSCH_2CH_2COONa$$

With regard to this conversion, it is necessary to decrease the amount of water existing in the resultant solution by raising a reaction temperature up to about 130° C. The reason for this is that the above reaction is difficult to proceed at a temperature below 120° C.

As thus obtained alkaline β-mercaptopropionate is acidified with a strong acid such as sulfuric or hydrochloric acid, β-mercaptopropionic acid is prepared as follows:

$$NaSCH_2CH_2COONa + H_2SO_4 \rightarrow HSCH_2CH_2COOH + Na_2SO_4\text{(recovery)}$$

Preferably, the reaction vessel used is glass-made as the obtained β-mercaptopropionic acid is hardly lost by oxidation. In order to prevent the oxidation, inertive gas may be filled up when an iron-made vessel is used.

According to the method of this invention, β-mercaptopropionic acid may be easily prepared from thiodipropionic acid by adding alkaline thiodipropionate to high concentration of aqueous solution of alkaline sulfide and then reacting the mixed solution at 110° to 130° C. for a short period only. In the other course of this invention, it is also possible to employ excess of alkaline hydroxide. The other course is more economical than the original course because an amount of the low-priced alkaline hydroxide used increases and an amount of the high-priced alkaline sulfide used decreases. The other course also can get a higher productivity of β-mercaptopropionic acid than the original course.

With respect to the production cost and the yield of β-mercaptopropionic acid, the method according to this invention is not much different from my old method using acrylonitrile and sodium sulfide, as disclosed in Japanese Patent Publication No. 6545/88. However, it is possible to prepare a large amount of β-mercaptopropionic acid efficiently and cheaply when the method is practiced jointly with my old method mentioned above. Furthermore, the method is more successful for a reduction of the by-products in quantity.

According to the modification of the method, it is possible to prepare β-mercaptopropionic acid more easily as a whole and to raise an efficiency of the operation. The reason for this is that it is unnecessary to isolate residual alkaline thiodipropionate from the reacted solution. When residual alkaline thiodipropionate is converted into alkaline β-mercaptopropionate, it is only necessary to decrease an amount of water existing in the reacted solution by raising the reaction temperature up to about 130° C. The modification of the method has the advantage of economization because the process of production is simpler and the time required for the total reaction is shorter. Relating to this modification, since an amount of the water added decreases, it is possible to increase the total quantity of the raw materials. Furthermore, a treatment of drainage is simpler and thus a problem of environmental pollution can hardly happen.

β-mercaptopropionic acid prepared by this invention is much in demand for cross-linking agents for acrylic ester polymer, hardening agents for epoxy resin, raw materials of synthetic resin for lens, stabilizers for polyvinyl chloride and the like and the production thereof still increases extensively. As described in Japanese Patent Publication No. 6545/88, thiodipropionic acid generated as the by-product has been useful as stabilizers or antioxidants. However, the demand thereof has a decreasing tendency in this application because another very low-priced chemical compound has been beginning to be used recently. It is obvious that thiodipropionic acid can be consumed as the starting material of the method according to this invention, even if it is extremely probable that the disposal of thiodipropionic acid becomes increasingly difficult to in the future.

The invention will be understood more readily with reference to the following example, and variations may be made by one skilled in the art without departing from the spirit and scope of the invention.

EXAMPLE 1

30 grams of thiodipropionic acid and 40 grams of 33% sodium hydroxide were mixed to generate sodium thiodipropionate. This sodium salt was added to the aqueous solution of sodium sulfide produced by mixing 40 grams of sodium hydrosulfide, 60 grams of 33% sodium hydroxide and 20 grams of water with heating, which was then heated to raise the solution temperature to 123° C.

The mixed solution was reacted at 120° to 130° C. for 1 hour, and then poured into a solution of 80 grams of 62% sulfuric acid and 350 cm³ of water. The reacted solution was boiled for 2 to 3 minutes until hydrogen sulfide generated during the reaction was flown about in the air. Finally, the solution was cooled and then extracted with dipropyl ether.

The volume of the solution obtained was made up exactly to 1000 cm³ by adding water. 10 cm³ of the resultant solution was taken in a hole pipet and dropped into 1/10N iodine from the pipet in order to hold an iodometric titration. The consumption of an indicator (starch solution) was 24.7 cm³. As this result, it was proved that the weight of the β-mercaptopropionic acid obtained was 26.7 grams. This yield reached about 89% based upon the amount of the thiodipropionic acid employed and was close to 75% of the theoretical amount.

EXAMPLE 2

98 grams of 33% sodium hydroxide were added to 72 grams of thiodipropionic acid to generate sodium thiodipropionate. This sodium salt was added to the aqueous solution of sodium sulfide produced by dissolving 125 grams of 60% flaky sodium sulfide in 60 cm³ of water with addition of heating, and then heated to raise the solution temperature.

The mixed solution was reacted at 123° to 127° C. for 2.5 hour, and then poured into the solution of 260 grams of 62.5% sulfuric acid and 200 cm³ of water with stirring. The reacted solution was cooled and filtered to remove mirabilite separated as crystals at 40° C. The filtrate was extracted 4 times with 100 cm³ of dipropyl ether. On the other hand, the deposited mirabilite was washed twice with 100 cm³ of dipropyl ether, and the washings and the extractives were combined into one. After the combined dipropyl ethers had been recovered by distillation at room temperature, 55 grams of β-mercaptopropionic acid (98.1% purity) were obtained by distillation at reduced pressure of 10 mm Hg.

Also, 15 grams of unreacted crude thiodipropionic acid were recovered from the residue that remained in the flask.

EXAMPLE 3

220 grams (about 1.2 mol) of thiodipropionic acid and 430 grams (about 5.1 mol) of 47% sodium hydroxide were added and dissolved in 300 cm³ of water to generate sodium thiodipropionate. Then 280 grams (about 2.2 mol) of 60% sodium sulfide were added to the solution and the reaction was carried out at 130° C. for 1 hour. When the resultant solution was acidified by adding 500 cm³ of water and 460 cm³ of 62.5% sulfuric acid, an oily substance was separated. The residual solution was extracted 4 times with 200 grams of isopropyl ether. The total extractives were combined into one and the isopropyl ether was recovered by distillation at reduced pressure.

When the oily crude β-mercaptopropionic acid and the residue after the distillation of the ispropyl ether were combined into one, 235 grams of β-mercaptopropionic acid were obtained (exchange rate 100). This yield was about 90% of the theoretical amount.

EXAMPLE 4

110 grams of 70% sodium hydrosulfide and 60 grams of water were heated at 50° to 60° C. and then 53 grams of acrylonitrile were dropped into the solution in the period of about 30 minutes. After the dropping, this solution was reacted at 50° to 60° C. for 1 hour. Subsequently, 172 grams of 47% sodium hydroxide was added to the solution little by little. When the solution was heated gradually after the addition, ammonia gas was flown at about 80° C.

The mixed solution was reacted at 130° to 133° C. for about 1 hour, and then 330 grams of 62% sulfuric acid were added to acidify the solution. When the reacted solution was cooled to 40° C. and crude β-mercaptopropionic acid was separated from the solution, the weight of the acid was 140 grams. By an analysis using an iodometric titration, it was proved that the obtained β-mercaptopropionic acid was 68 grams as the yield of the acid reached 48.9%. On the other hand, water was added to the residual solution including mirabilite and the volume thereof was made up exactly to 1000 cm³. By an analysis using an iodometric titration after dissolving the mirabilite by heating, it was proved that the existence of 15 grams of β-mercaptopropionic acid was recognized as the content of the acid was 1.5% in the solution.

As this result, the combined yield of β-mercaptopropionic acid reached 83 grams. This yield was close to 78.3% of the theoretical amount.

What is claimed is:

1. A method for making β-mercaptopropionic acid, which comprises:

adding alkaline hydroxide to thiodipropionic acid isolated in the solid state to generate alkaline thiodipropionate; mixing thus obtained alkaline thiodipropionate with an aqueous solution of alkaline sulfide;

heating the mixed solution to the temperature that a reaction takes place, and acidifying the resultant solution with a strong acid.

2. A method for making β-mercaptopropionic acid, which comprises: adding excess alkaline hydroxide to thiodipropionate acid, the reaction of the obtained alkaline thiodipropionate and an aqueous solution of alkaline sulfide takes place in the presence of the residual alkaline hydroxide that remains in the reacted solution, heating the mixed solution to the temperature that a reaction takes place and acidifying the resultant solution with a strong acid.

* * * * *

UNITED STATES PATENT AND TRADEMARK OFFICE
CERTIFICATE OF CORRECTION

PATENT NO. : 5,256,818

DATED : October 26, 1993

INVENTOR(S) : Tomioka

It is certified that error appears in the above-identified patent and that said Letters Patent is hereby corrected as shown below:

Column 1, Line 28, after "6545/88" insert -- hereby incorporated by reference --

Signed and Sealed this

Fifth Day of April, 1994

Attest:

BRUCE LEHMAN

Attesting Officer

Commissioner of Patents and Trademarks